(12) United States Patent
Jun (10) Patent No.: US 7,604,630 B2
(45) Date of Patent: Oct. 20, 2009

(54) APPLICATOR ATTACHABLE TO SKIN TREATMENT DEVICE AND SKIN TREATMENT METHOD USING THE SAME

(76) Inventor: Yong Gyu Jun, 26-801, Slyeong Apt., 450 Seongsan-Dong, Mapo-Gu, Seoul 121-250 (KR)

( * ) Notice: Subject to any disclaimer, the term of this patent is extended or adjusted under 35 U.S.C. 154(b) by 0 days.

(21) Appl. No.: 11/707,206

(22) Filed: Feb. 15, 2007

(65) Prior Publication Data

US 2007/0203447 A1   Aug. 30, 2007

(30) Foreign Application Priority Data

| Feb. 28, 2006 | (KR) | ................ 10-2006-0019228 |
| Jun. 28, 2006 | (KR) | ................ 10-2006-0058533 |
| Jan. 8, 2007 | (KR) | ................ 10-2007-0001940 |

(51) Int. Cl.
*A61B 18/18* (2006.01)
*A61N 5/06* (2006.01)

(52) U.S. Cl. .................................. 606/9; 607/89

(58) Field of Classification Search ............ 604/20; 607/88, 89, 100, 101; 606/9
See application file for complete search history.

(56) References Cited

U.S. PATENT DOCUMENTS

| 6,071,239 | A * | 6/2000 | Cribbs et al. ............... 600/439 |
| 6,169,926 | B1 * | 1/2001 | Baker .......................... 607/99 |
| 6,273,884 | B1 * | 8/2001 | Altshuler et al. .............. 606/9 |
| 6,461,354 | B1 * | 10/2002 | Olsen et al. ................. 606/41 |
| 6,508,813 | B1 * | 1/2003 | Altshuler ....................... 606/9 |
| 6,511,475 | B1 * | 1/2003 | Altshuler et al. .............. 606/9 |
| 6,517,532 | B1 * | 2/2003 | Altshuler et al. .............. 606/9 |
| 6,595,934 | B1 * | 7/2003 | Hissong et al. ............... 601/3 |
| 6,605,080 | B1 * | 8/2003 | Altshuler et al. .............. 606/3 |
| 6,652,518 | B2 * | 11/2003 | Wellman et al. ............. 606/41 |
| 6,662,054 | B2 * | 12/2003 | Kreindel et al. ............ 607/101 |
| 6,663,618 | B2 * | 12/2003 | Weber et al. ................... 606/2 |
| 6,663,622 | B1 * | 12/2003 | Foley et al. .................. 606/34 |
| 6,676,655 | B2 * | 1/2004 | McDaniel ...................... 606/9 |
| 6,702,808 | B1 * | 3/2004 | Kreindel ........................ 606/9 |
| 6,725,095 | B2 * | 4/2004 | Fenn et al. .................. 607/101 |
| 6,766,202 | B2 * | 7/2004 | Underwood et al. .......... 607/99 |
| 7,217,265 | B2 * | 5/2007 | Hennings et al. ............... 606/9 |
| 7,250,047 | B2 * | 7/2007 | Anderson et al. ............ 606/32 |
| 2002/0133152 | A1 * | 9/2002 | Strul ........................... 606/50 |
| 2002/0143326 | A1 * | 10/2002 | Foley et al. .................. 606/41 |
| 2003/0004454 | A1 * | 1/2003 | Fenn et al. .................... 604/20 |
| 2003/0027186 | A1 * | 2/2003 | Pierce ........................... 435/6 |

(Continued)

*Primary Examiner*—Kevin C Sirmons
*Assistant Examiner*—Michael J Anderson
(74) *Attorney, Agent, or Firm*—GWiPS (57) ABSTRACT

An applicator attachable to a skin treatment device that is capable of simultaneously applying RF energy and optic energy to a patient's skin, and a skin treatment method using the applicator are developed. The skin treatment device comprises: a housing, one or pair of electrodes arranged inside of the housing for generating the high frequency waves, a suction cavity formed in front of the electrodes while it is contacting to the patient's skin, opposite end installed to the housing and an lateral vacuum pocket that is connected to a flow pathway connected to a vacuum system for generating negative pressure inside the applicator. Thus, the patient's skin is lifted by suction force to place between the pair of electrodes for easily and effectively penetrating the laser beams in to the dermis.

10 Claims, 8 Drawing Sheets

U.S. PATENT DOCUMENTS

| | | | |
|---|---|---|---|
| 2003/0028186 A1* | 2/2003 | Kreindel | 606/41 |
| 2003/0055471 A1* | 3/2003 | Fenn et al. | 607/101 |
| 2003/0130575 A1* | 7/2003 | Desai | 600/417 |
| 2004/0059282 A1* | 3/2004 | Flock et al. | 604/20 |
| 2004/0220512 A1* | 11/2004 | Kreindel | 604/20 |
| 2004/0260210 A1* | 12/2004 | Ella et al. | 601/7 |
| 2005/0049543 A1* | 3/2005 | Anderson et al. | 604/20 |
| 2005/0107870 A1* | 5/2005 | Wang et al. | 623/1.44 |
| 2005/0203593 A1* | 9/2005 | Shanks et al. | 607/89 |
| 2005/0222555 A1* | 10/2005 | Manstein et al. | 606/9 |
| 2006/0004306 A1* | 1/2006 | Altshuler et al. | 601/3 |
| 2006/0004347 A1* | 1/2006 | Altshuler et al. | 606/4 |
| 2006/0020309 A1* | 1/2006 | Altshuler et al. | 607/88 |
| 2006/0058712 A1* | 3/2006 | Altshuler et al. | 601/15 |
| 2006/0094988 A1* | 5/2006 | Tosaya et al. | 601/2 |
| 2006/0095096 A1* | 5/2006 | DeBenedictis et al. | 607/88 |
| 2006/0265032 A1* | 11/2006 | Hennings et al. | 607/89 |
| 2007/0010861 A1* | 1/2007 | Anderson et al. | 607/96 |

* cited by examiner

APPLICATOR ATTACHABLE TO SKIN TREATMENT DEVICE AND SKIN TREATMENT METHOD USING THE SAME

BACKGROUND OF THE INVENTION

1. Field of the Invention

The present invention relates to an applicator attachable to a skin treatment device and a skin treatment method using the applicator. More particularly, the applicator attachable to the skin treatment device, being capable of simultaneously applying RF energy and diode laser energy, provides a means to lift the skin via suction and place it between the electrodes to allow the high frequency rays to effectively penetrate and form collagens in the deep dermis.

2. Description of the Related Art

Commonly, a skin treatment device is used for removing tiny wrinkles, acne scars, acnes, pore contractions, darkened age spots and hairs for improving skin conditions such as skin color or skin organs.

Figure 1:
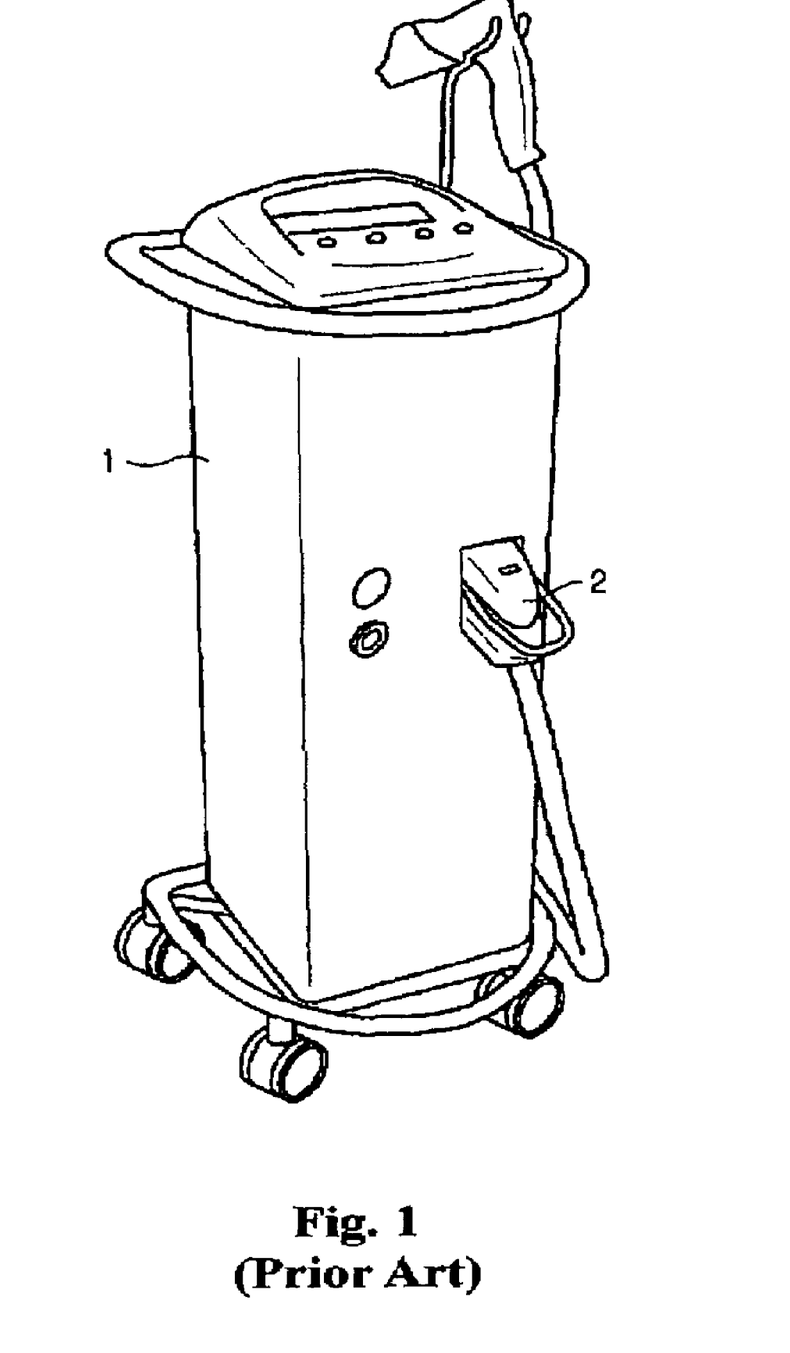
FIG. 1 is a schematic drawing of a conventional skin treatment device.

As shown in FIG. 1, a conventional skin treatment device is equipped with a separate applicator, which is connected to the main body for simultaneously applying the RF energy and diode laser energy.

Figure 2:
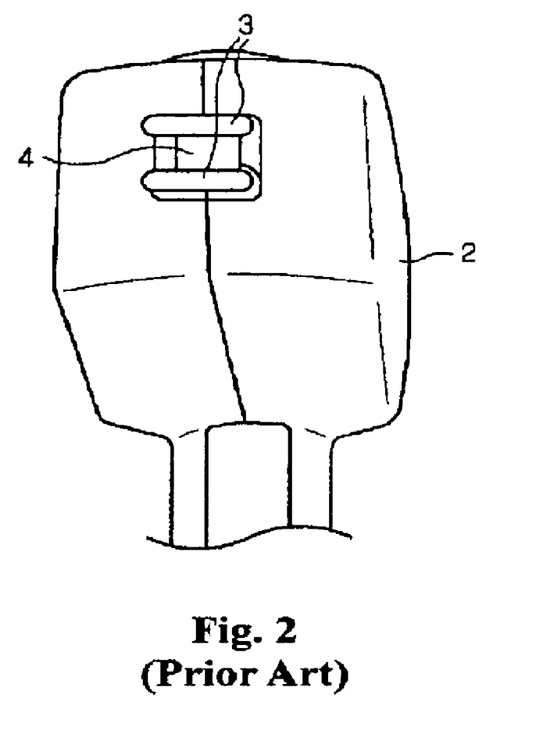
FIG. 2 is a schematic drawing obliquely showing an applicator of the conventional skin treatment device.

As shown in FIG. 2, the conventional applicator (2) has a front tip portion with a pair of electrodes (3) for emitting the high frequency radiation. The electrodes (3) installed in the front tip portion protrude from the applicator (2) for directly contacting the skin. A transparent permeating element (4) called a crystal is installed between the pair of electrodes (3) as a flow path of the diode laser beam.

Figure 3:
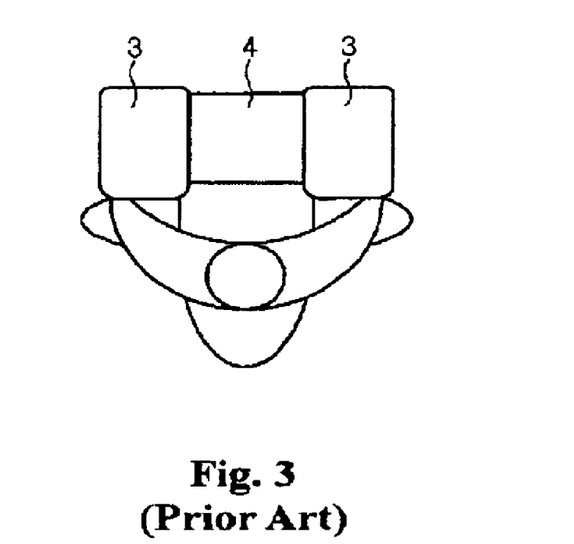
FIG. 3 is a conceptual drawing showing the conventional applicator positioned to contact a patient's skin for treatment.

As shown in FIG. 3, the high frequency waves flowing between the pair of electrodes (3) and diode laser beams penetrate into the dermis to form a heating spot. Because of the heating spot formed by the concentrated heat energy, it will effectively produce collagen in the dermis.

In order to effectively improve the skin treatment, it is important to develop the heating spot in the dermis. To do so, it is favorable to place the patient's skin between the pair of electrodes (3).

Because the epidermis has relatively higher impedance, but the dermis has relatively lower impedance, and the pair of electrodes (3) protrudes from the front tip portion of the applicator (2), the skin treatment is performed under such poor conditions that the patient's skin is forcibly depressed by the pair of electrodes (3). It often causes the patient to feel discomfort and pain during the skin treatment.

Furthermore, occasionally burns or skin damage can occur because of the excessive heating, stimulation or depression for forcibly and quickly producing collagen in the dermis, while using the high frequency waves flowing between the pair of electrodes (3) and diode laser beams.

SUMMARY OF THE INVENTION

In order to overcome the aforementioned conventional problems, the first purpose of the present invention is to provide a skin treatment device adopting an applicator and a skin treatment method using the applicator. The applicator attachable to the skin treatment device is provided with a vacuum cavity for sucking up the patient's skin between the pair of electrodes in order to eliminate any unpleasant feelings or pain during the skin treatment.

The second purpose of the present invention is to focus the effective treatment in the dermis while maximizing the cooling efficiency for not only maintaining a moderate skin temperature, but also preventing possible skin burns. When the high frequency wave flows between the pair of electrodes, heat is generated at each electrode. If excessive heat is generated, it may cause the patient's skin to burn. Thus, it is necessary to precisely control the electrode temperature to prevent possible damage to the patient.

The third purpose of the present invention is to form a hot spot in the dermis by illuminating a specific frequency of optical energy onto the patient's skin for maximizing the skin treatment effect. The laser beam of 915 nm is suitable to use for the optical energy. A heating spot is formed by concentrating the heat energy from the high frequency wave flowing between the pair of electrodes (3) and diode laser beams penetrating the dermis. Therefore, the heating spot will effectively produce collagen in the dermis.

The fourth purpose of the present invention is to provide a relief process after the skin treatment by emitting a specific frequency wave. The treated skin builds up stress and tension because of the stimulation during the skin treatment. Therefore, the relief process cures the skin organs to be stable and prevents possible skin damage by relieving the stress and tension. A red light is suitable for the specific frequency wave.

The fifth purpose of the present invention is to provide an applicator attachable to the skin treatment device. Therefore, it is possible to replace the front tip portion of the applicator for handling various kinds of devices, such as the high frequency wave, medium-lower frequency waves, ion inducement, skin membrane treatment, fat-fusion, and skin care or fat-control treatment.

For achieving the aforementioned first objective of the present invention, an applicator attachable to a skin treatment device is provided, comprising: a housing (11) for protecting inner mechanisms, one or more electrodes (14) that are arranged inside of the housing for generating high frequency waves, and a capsule (23) forming a suction cavity (16) at an inlet portion, in which one end of the electrode (14) contacts a patient's skin and the opposite end of the electrode (14) is attached to the housing, an inner space (17) connected to the suction cavity (16), and a flow passage (21) for interconnecting between a vacuum unit and the internal space (17) for generating a negative pressure in the inner space, and wherein the electrode is partially exposed between one end and the opposite end.

Herein, a pair of electrodes (14) is arranged inside of the housing for emitting a high frequency wave to the patient epidermis. On the other hand, a single electrode (14) can be arranged inside of the housing without a ground connection.

Further, a filter (22) is provided on the flow passage (21) for preventing foreign objects on the patient's skin from being sucked in.

For achieving the aforementioned second objective of the present invention, a cooling unit (15) is provided in the housing (11) for removing the heat generated by the electrode. The cooling unit comprises a thermocouple (15a) tightly surrounding the pair of electrodes (14) and a cooling block (15b) tightly surrounding the thermocouple (15a).

For accomplishing the aforementioned third objective of the present invention, a diode infrared laser (12) is installed in the housing (11) for emitting a near infrared laser beam of 800~1,000 nm. Further, a permeating element is installed in front of a diode infrared laser for permeating the infrared laser beam. The preferred wavelength for the near infrared laser beam is 915 nm.

To achieve the aforementioned fourth objective of the present invention, a three-color emitting diode (31) is obliquely installed on the lateral side of the permeating element (13) in the housing (11) for selectively emitting either blue light, red light or infrared light. A reflecting element (32)

is also installed at the opposite side of the three-color emitting diode (31) to reflect the emitted lights. It is preferred that the three-color emitting diode (31) emits red light with a wavelength of 630 nm to 640 nm.

For achieving the aforementioned fifth objective of the present invention, the housing (11) comprises a first mounting block (41) for coupling a capsule (23), a second mounting block (43) for coupling the first mounting block (41) at the front and the housing (11) at the rear, wherein the capsule (23) is formed with a female thread (23a) near its inner rim and the first mounting block (41) is formed with a male thread (41a) at the front portion for threading into the female thread (23a) of the capsule (23).

Further, the first mounting block (41) is formed with a flange (41b) at the rear. The second mounting block (43) is formed with a front annular groove (43a) for elastically coupling with the flange (41b) of the first mounting block (41).

On the other hand, the second mounting block (43) is formed with a rear annular groove (43a), and the front portion of the housing (11) is formed with a tip flange (11a) for elastically coupling with the rear annular groove (43a) of the second mounting block (43).

The capsule (23) comprises a lateral vacuum pocket (25) being connected to the flow passage (21), the first mounting block (41) consisting of a tube plug (51a) having a first flow path (51) connected to the lateral vacuum pocket (25), and the second mounting block (43) consisting of an extension tube (53a) having a second flow path (53) for connecting to the first flow path (51) of the tube plug (51a).

To achieve another objective of the present invention, a skin treatment method using an applicator attachable to a skin treatment device is provided, the method comprising the following steps: the applicator is applied to a patient's skin to form a negative pressure in a suction cavity (16) at the inlet portion; an electrode (14) installed in the housing is warmed up and a negative pressure is generated in the inner space (17) by a vacuum that is connected through the suction cavity (16) and a flow passage (21); (a) the patient epidermis is partially sucked into a suction cavity (16); and (d) the high frequency wave is projected onto the patient skin, while the patient's skin is being lifted and massaged.

Further, a cooling process may be added between the above (a) step and (d) step for (b) cooling the patient's skin to protect it from possible overheating.

To achieve the further objective, an illuminating step can be added prior to step (d): (c) the near infrared beam in the range of 800 nm~1,000 nm emitted by a diode laser (12) is illuminated onto the patient's skin through a permeating element (13). At this point, it is preferred to use the near infrared beam with a wavelength of 915 nm. Alternatively, a further step is recommended that: (e) a red light beam in the range of 630~660 nm is illuminated onto the patient's skin.

BRIEF DESCRIPTION OF THE DRAWINGS

FIGS. 8 to 10 are the mimetic diagrams illustrating each step of the skin treatment of the present invention.

DESCRIPTION OF THE PREFERRED EMBODIMENTS

According to the present invention, an applicator attachable to the skin treatment device sucks up a certain amount of the patient's skin into a vacuum cavity, which is located between a pair of electrodes at the front tip of the applicator. Due to the technique of skin lifting, the skin is exposed closer to the optical energy source. Thus, the emitted optical energy can penetrate deeply into the patient's dermis. Thereby it is possible to perform better skin treatment, such as the treatment of the skin organ, blood vessel, pigment, hair root and pores, than with the conventional method. It also has advantages of consuming less optical energy and performing safer treatment than the conventional method.

Because a constant vacuum pressure is applied to lift the skin via suction, the blood stream is steadily maintained closer to the epidermis. This phenomenon enhances the absorbing rate with prompt reaction during the skin treatment. Thus, it is possible to efficiently obtain a clinical effect and consume less optical energy compared to the conventional method.

Accordingly, the skin sucked up by the vacuum pressure will not be irritated or painful for the patient. Because of the enhanced absorbing rate, a local heat spot quickly develops in the dermis even if emitting relatively lower optical energy compared to the conventional method. The RF wave is suitable to easily induce the reaction of the local hot spot by concentrating the optical energy into the dermis.

As discussed so far, the skin treatment device of the present invention has merits that it has effectively developed Collagen by escalating the heat in the dermis without irritation or pain, for the purpose of removing the tiny wrinkles, pores and scars.

Further, the present skin treating device is able to improve the clinical effect because of the stable energy values. The device is designed to be simple and comfortable to operate, so it is possible to render an effective treatment and minimize the possible side effects from the high frequency spark.

During the skin treatment operation, extra precautions must be taken around the sensitive areas in the body, such as around the cheek, bone protruded parts, near teeth, and around eyes. For treating those areas, it is necessary to lift the skin a certain distance away from the sensitive organs by the constant vacuum pressure. Thus, it is possible to perform the stable treatment while avoiding or minimizing the side effects due to the emitted RF beams.

It has more advantages to affect the contracting pores and to mitigate scars. Because the pores and the scar organs are momentarily expanded while the skin is lifted up by vacuum suction, the emitted optical energy effectively permeates more and deeper into the dermis.

Because the skin treatment device of the present invention is simultaneously sucking and treating the patient's skin by emitting the RF optical energy, it provides operational stability, convenience, and efficiency while minimizing the side effects.

IMPLEMENTING EXAMPLE 1

Hereinafter, the applicator attachable to the skin treatment device according to the first embodiment of the present invention is described in detail with reference to the accompanying drawings.

Figure 4:
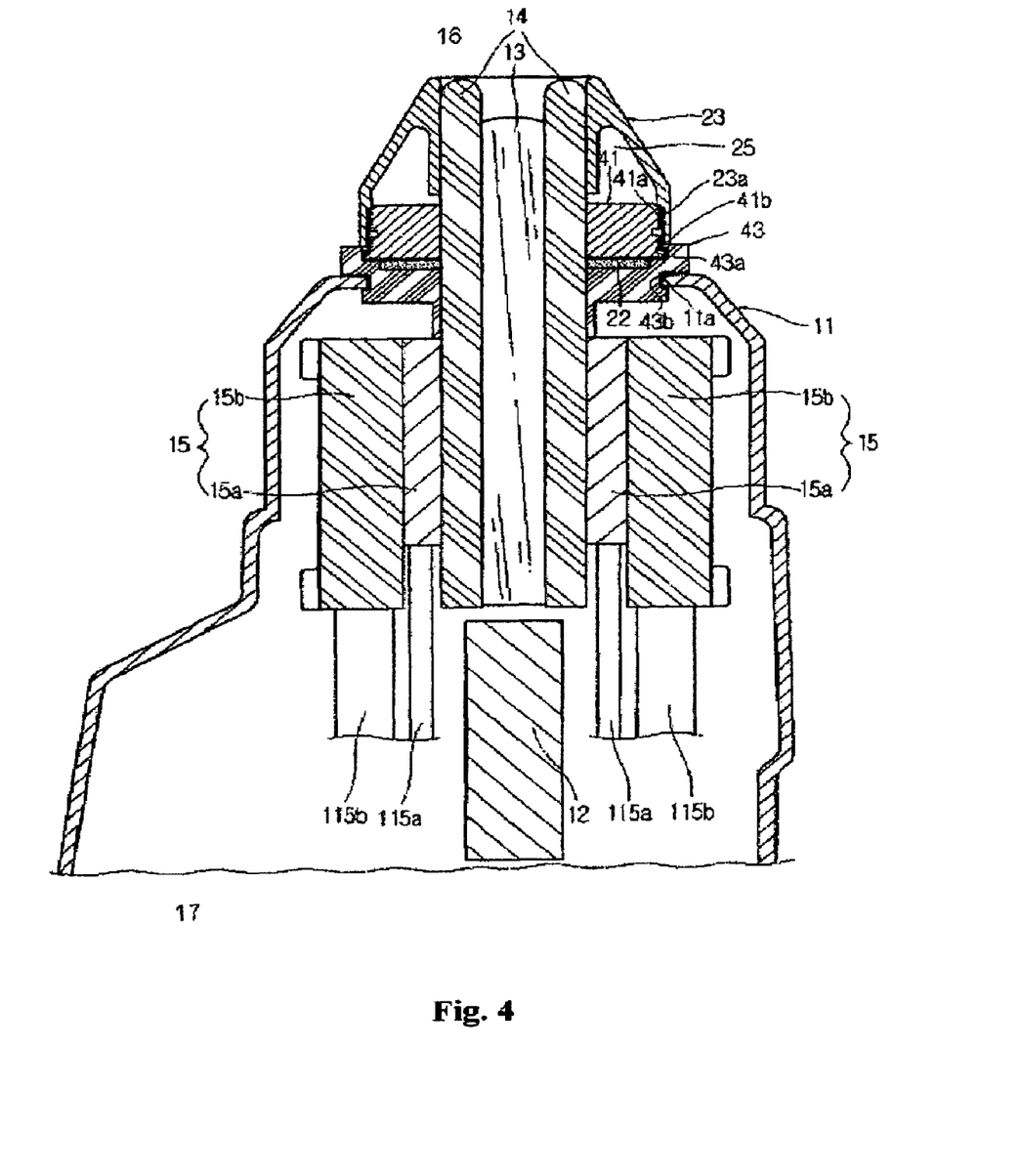
FIG. 4 is a front cross-section of a skin treatment applicator according to the first embodiment of the present invention.
Figure 5:
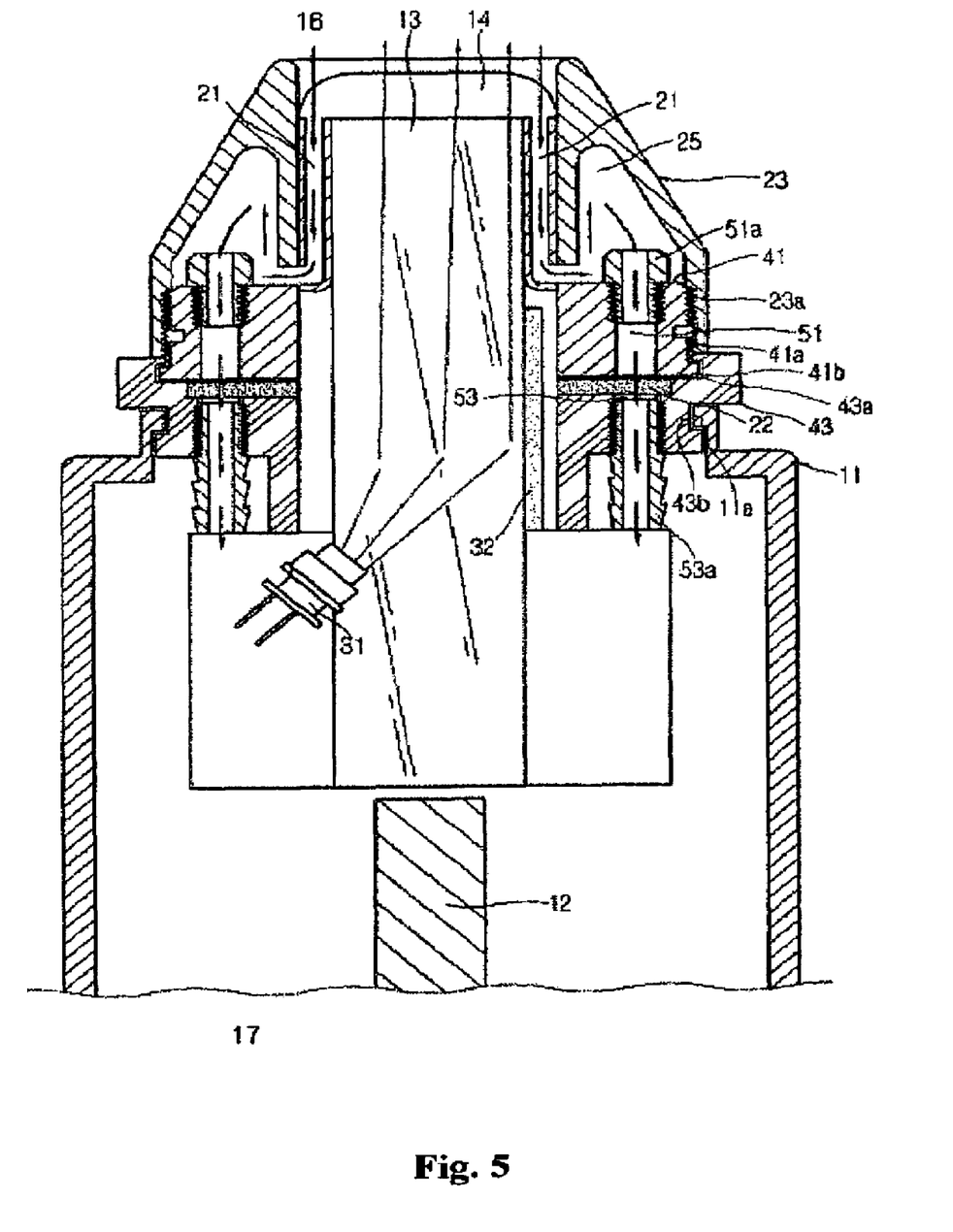
FIG. 5 is a side cross-section of a skin treatment applicator according to the first embodiment of the present invention.

Accordingly, FIG. 4 is a front cross-section of the applicator attachable to the skin treatment device according to the first embodiment of the present invention. FIG. 5 is a side cross-section of the applicator attachable to the skin treatment device according to the first embodiment of the present invention.

As shown in FIGS. 4 and 5, the applicator attachable to the skin treatment device of the first embodiment of the present invention comprises mainly a housing (11), a diode laser emitter (12), a permeating element (13), a pair of electrodes (14) and a cooling unit (15).

Though the overall features of the housing (11) are shaped like a handgun, only the front portions of the housing and capsule are shown in the presented drawings.

The diode laser emitter (12), which is partially shown in the drawing is installed inside of the housing (11) for emitting the laser beams in the range of 915 nm.

The permeating element (13) made of transparent crystal is installed in front of the diode laser emitter (12) acting as a permeating path for the laser beams.

The pair of electrodes (14) is installed to both sides of the permeating element (13) for generating the high frequency. The pair of electrodes (14) protrudes slightly farther than the permeating element (13). The pair of electrodes (14) and the permeating element (13) are arranged at the front tip of the applicator that is the portion to contact the patient's skin. The diode laser beam that is the high frequencies flowing between the pair of electrodes (14) and passing through the permeating element (13) penetrates into the dermis. The heat energy is concentrated to form a hot spot for producing the Collagen in the dermis.

The cooling unit (15) comprising a thermocouple (15a) tightly surrounding the pair of electrodes (14) and a cooling block (15b) tightly surrounding the thermocouple (15a) for removing the heat generated by the electrodes (14).

The cooling block (15b) closely arranged outside of the thermocouple (15a) is connected to a coolant passage (115b). The coolant passage (115b) is connected to the cooling system.

Accordingly, the pair of electrodes (14) attached each thermocouple (15a) is connected to the cooling block (15b). Thus, the heat generated by the pair of electrodes (14) is effectively removed to avoid burns during the skin treatment.

Further, the thermocouple (15a) is connected to a controlling unit of the main body for controlling the temperature of the pair of electrodes (14) by controlling the amount of coolant circulated in the cooling block (15b).

On the other hand, the applicator attachable to the skin treatment device of the present invention comprises a capsule (23) located in front of the pair of electrodes (14) and the housing (11). The capsule (23) is formed with a flow passage (21) surrounding the pair of electrodes (14) and extending to the rear portion of the housing.

Further, the housing (11) comprises the first mounting block (41) and second mounting block (43) for coupling the capsule (23). The capsule (23) is formed with a female thread (23a) near its inner rim. The first mounting block (41) is formed with a male thread (41a) at its front portion for mating to the female thread (23a) of the capsule (23).

The first mounting block (41) is formed with a flange (41b) at its rear portion. The second mounting block (43) is formed with a front annular groove (43a) for elastically coupling to the flange (41b) of the first mounting block (41).

The second mounting block (43) is formed with a rear annular groove (43b) at its rear portion. The front portion of the housing (11) is formed with a tip flange (11a) for elastically coupling with the rear annular groove (43a) of the second mounting block (43).

According to the applicator of the first implementing example, a three-color emitting diode (31) is obliquely installed on the lateral side of the permeating element (13) for selectively emitting either blue light, red light or infrared light. On the opposite side of the three-color emitting diode (31), a reflecting element (32) is installed for reflecting the emitted light.

The capsule (23) is formed with a lateral vacuum pocket (25) connected to the flow passage (21). The first mounting block (41) consists of a tube plug (51a) having a first flow path (51) connected to the lateral vacuum pocket (25). The second mounting block (43) consists of an extension tube (53a) having a second flow path (53) for connecting to the first flow path (51) of the tube plug (51a). The extension tube (53a) is connected to the main vacuum system located outside of the housing. Accordingly, the capsule (23) is attached to or detached from the housing (11) for replacing different kind of capsule during the skin treatment.

Accordingly, the vacuum pressure is supplied through the second flow path (53), the first flow path (51), the vacuum pocket (25), and the flow passage (21) to the capsule (23) attached to the front tip of the housing (11) for creating negative pressure.

As the negative pressure is created in the capsule (23), the patient's skin is sucked to be lifted up and placed between the pair of electrodes (14).

Accordingly, it is not necessary for an operator to depress the applicator tightly against the skin, because the patient's skin is lifted up and placed between the pair of electrodes (14). It is also convenient to operate over the irregularly curved surface of the patient's skin, because the constant vacuum pressure is applied to suck up a constant amount of the skin. Therefore, it is possible to avoid the side effect of unpleasant feelings or pain because of the spark of RF waves, which is caused by the improper contacting of the applicator to the skin.

As the patient's skin is lifted up and placed between the pair of electrodes (14), the lower impedance of the high frequency energy or optical energy is transmitted to concentrate in the dermis to improve the treatment effect. It also has a massage effect as the skin is sucked up.

According to the applicator of the present invention, a three-color emitting diode (31) is obliquely installed laterally to the permeating element (13) for selectively emitting either blue light, red light or infrared light. The ultraviolet rays in the range of 405 nm ~420 nm can be used to treat infected acne.

For this purpose, blue light in the 415 nm range of the high power narrow band is used. The blue light is used in the range of 405 nm ~420 nm that is out of the range of the ultraviolet rays. Thus, this blue light won't hurt the normal skin.

The three-color emitting diode (31) emits red light in the range of 630 nm~669 nm, which has excellent absorption rate into the dermis. Thus, the red light is used to stimulate the blood circulation, activate cells, and improve metabolism. The red light also has the excellent effects of the skin hydration, calm, tranquility and cell reproduction.

The reflecting element (32) is installed at the opposite side of the three-color emitting diode (31) for reflecting the emitted light.

Herein, if the blue light is emitted onto the P-acne, the endogenous enzyme of Por-phyrin is produced through metabolism. As a result, it produces the Singlet Oxygen through the optical reaction, which has no effect on the normal skin but destroys the bacteria.

The Photo Dynamic Therapy (PDT) uses the Singlet Oxygen, which is produced by destroying the Por-phyrin enzyme through the metabolism to destroy the bacteria of P-acne. The red light has an effect of color therapy for stabilizing the skin organs. As mentioned above, the high frequency wave and the diode laser beam have a stabilization effect for the excited skin.

Herein, the red light, as distinct from the infrared ray, is a visible light in the narrow range of 630 nm ~660 nm, which is able to produce a powerful light used for Somatology through coherence. Alternately, the diode laser beam in the range of 635 nm to 655 nm can be used for the red light.

The infrared ray emitted by the three-color emitting diode penetrates into the skin for heating to reproduce new cells. It also helps to produce Collagen and Elastin to stimulate the corpulence cell or the gigantic cell for reproducing new cells. Thus, it has an effect to promptly cure scars and tiny wrinkles or discolorations. The infrared ray emitted by three-color emitting diode can be in the wavelength range of 800 nm~900 nm.

Accordingly, the beams are sequentially emitted to the patient's skin in the order of the blue light for sterilizing, red light for soothing and infrared light for reproducing new cells.

The emitting operation of the above procedure is periodically repeated on the patient's skin until new cells are reproduced or the damaged skin is healed.

IMPLEMENTING EXAMPLE 2

Hereinafter, the applicator attachable to the skin treatment device according to the second embodiment of the present invention is described in detail with reference to the accompanying drawings.

Figure 6:
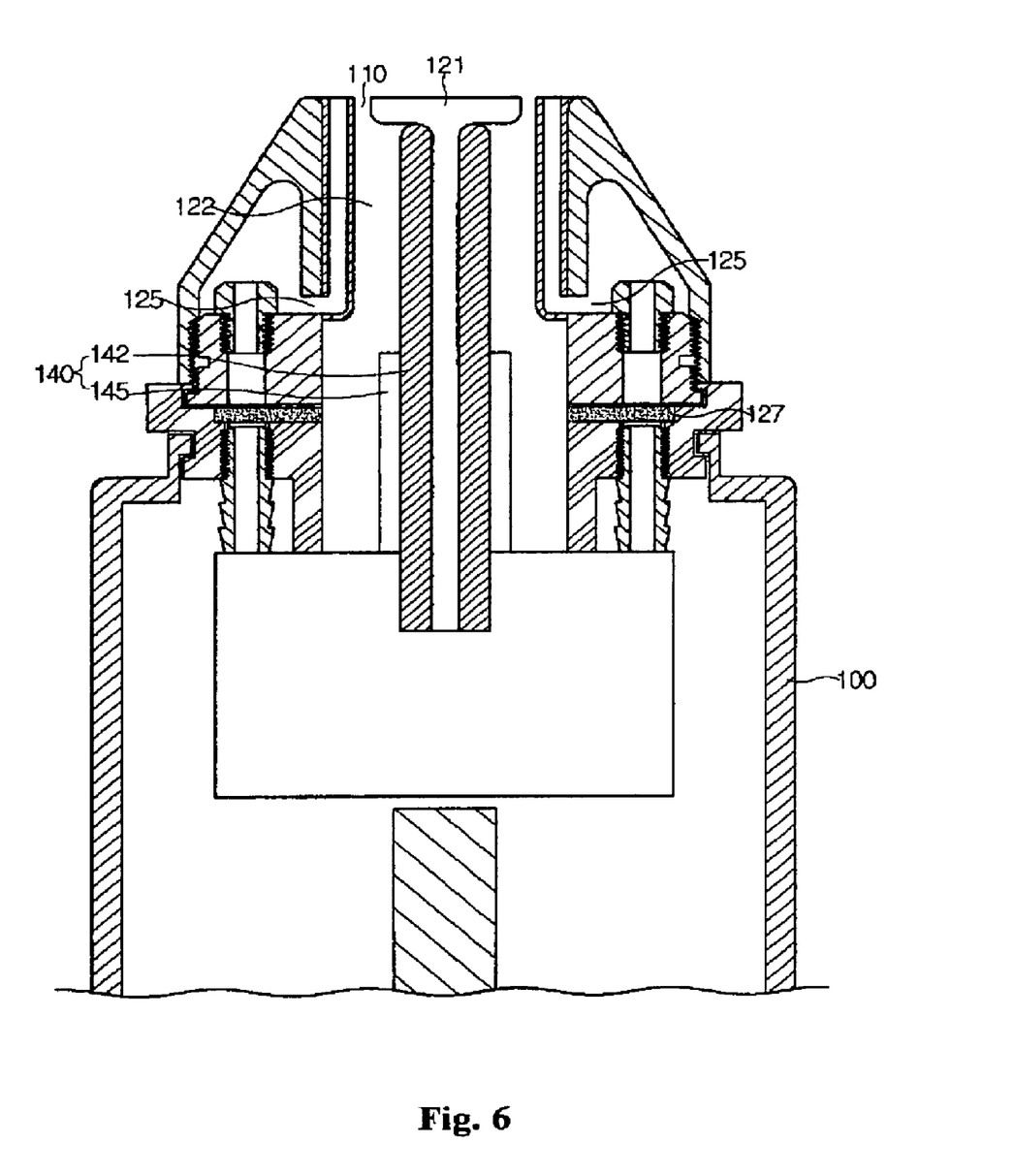
FIG. 6 is a side cross-section of a skin treatment applicator according to the second embodiment of the present invention.

Accordingly, FIG. 6 shows a side cross-section of an applicator attachable to the skin treatment device according to the second embodiment of the present invention.

As shown in FIG. 6, the applicator attachable to the skin treatment device of the second embodiment comprises: a housing (100) for protecting the inner mechanisms, a unipolar electrode (110) that is arranged inside of the housing for generating high frequency radiation, and a capsule (130) forming a suction cavity (121) at an inlet portion, which one end of the electrode (110) contacts a patient's skin and the opposite end of the electrode (110) is attached to the housing, an inner space (122) connected to the suction cavity (121), and a flow passage (125) for interconnecting between a vacuum unit and the inner space (122) for generating a negative pressure at the inner space, and wherein the electrode is partially exposed between one end and the opposite end.

Accordingly, the capsule (130) is mounted or removed from a tip portion of the hosing (100) for replacing different kind of capsule during the skin treatment.

Because the unipolar electrode (110) has a better capability to transmit the energy deeper into the dermis compared with the pair of electrodes, it is suitable to treat wrinkles and Cellulite.

As the negative pressure is developed in the capsule (130), the patient's skin is lifted up closer to the unipolar electrode (110). Because the high frequency energy penetrates deeply into the dermis, the skin treatment is effectively improved. Additionally, it has a massage effect due to the suction on the skin by the vacuum force.

Further, a filter (127) is installed on the flow passage (125) for preventing foreign objects on the patient's skin from being sucked into the vacuum system.

A cooling unit (140) is provided in the housing (11) for removing the heat generated by the electrode (110). The cooling unit (140) comprises a cooling block (142) surrounding both sides of the electrode (110) and a thermocouple (145) surrounding the cooling block (142).

Accordingly, the thermocouple (145) is connected to the power source to control the cooling temperature, while the cooling block (142) is effectively removing the heat generated by the electrode (110) to avoid burns during the skin treatment.

Hereinafter, a skin treatment method for applying the applicator attachable to the skin treatment device of the present invention is described in detail. The skin treatment device comprises: a housing (11) for protecting inner mechanisms, one or more electrodes (14) that are arranged inside of the housing for generating high frequency radiation, and a suction means forming a suction cavity (16) by contacting a patient's skin at one end of the electrode (14), the opposite end of the electrode (14) being attached to the housing to connect to the suction cavity. As needed, the skin treatment device may included: a cooling unit for removing the heat generated by the electrode, a diode laser beam emitter (12) for emitting near infrared rays of 800 nm~1,000 nm, and a permeating element (13) installed in front of the diode laser emitter (12) for permeating the emitted laser beams.

Figure 7:
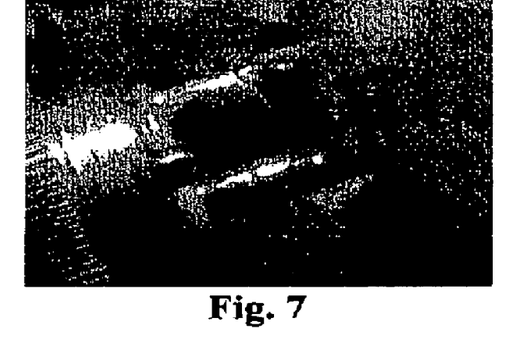
FIG. 7 is a photo showing a practical skin treatment by the skin treatment applicator of the present invention.
Figure 8:
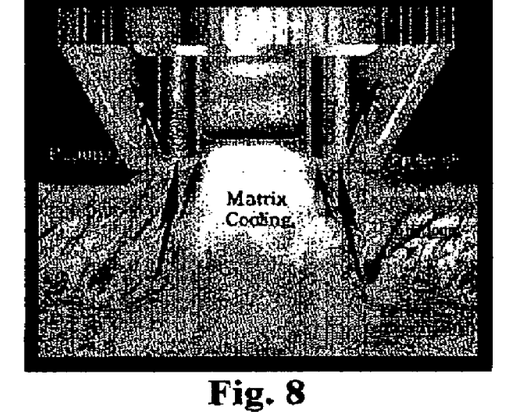
FIG. 8 is a mimetic diagram illustrating a step of suction and cooling.
Figure 9:
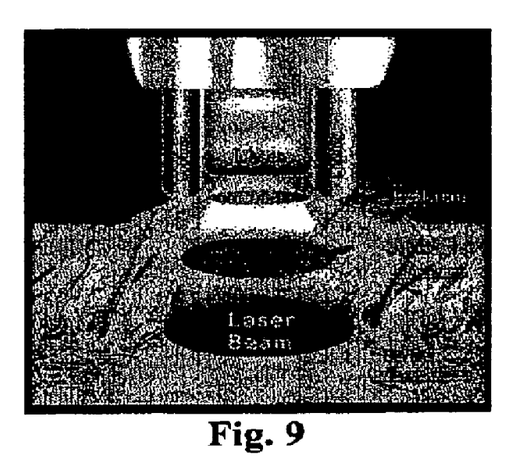
FIG. 9 is a mimetic diagram illustrating a step of suction and laser beam illumination.
Figure 10:
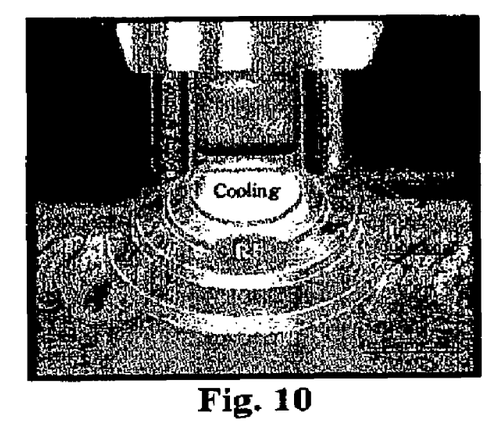
FIG. 10 is a mimetic diagram illustrating a step of suction and RF high frequency illumination.

FIG. 7 shows a photo of a practical skin treatment by the skin treatment applicator of the present invention. Referring to FIGS. 8 to 10, each step of skin treatment shown in the mimetic diagrams is examined.

As shown in FIG. 8, (a) a portion of the patient's epidermis is sucked up into the suction cavity (16) by the suction means, and (b) the lifted patient's skin is cooled down to about 0~10° through the cooling process for protecting the skin.

As shown in FIG. 9, (c) a diode laser beam emitter (12) emits the near infrared beam in the range of 800 nm~1,000 nm through a permeating element (13) onto the patient's skin. It is preferred to use the near infrared beam of 915 nm wave length to emit onto the patient's skin.

Figure 13:
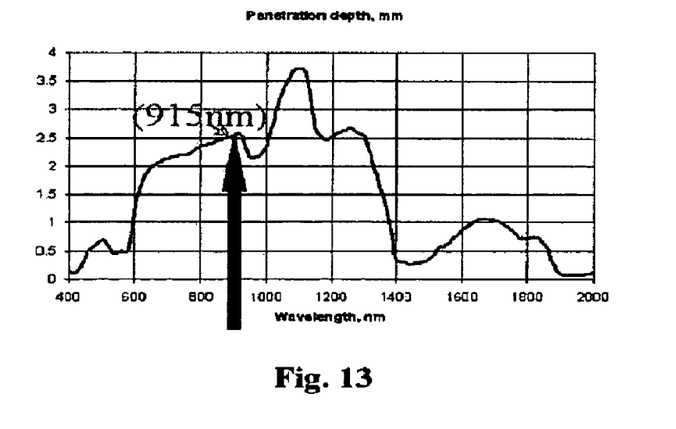
FIG. 13 is a graph illustrating the penetration depth depending on the wavelength of the laser beam.
Figure 14:
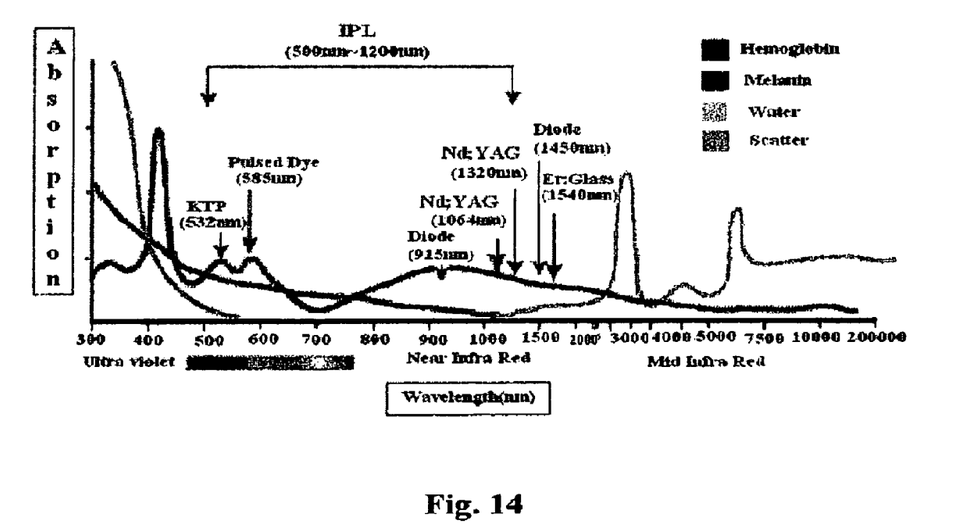
FIG. 14 is a graph illustrating a skin Chromophore depending on the wavelength of the laser beam.

As seen in FIGS. 13 and 14, the laser beam has a good absorption rate into the hemoglobin in the capillary vessels of the dermis compared to other Chromophores. Thus, the laser beam is suitable to perform the thermal stimulation of the selected area of the dermis to reproduce the new cells.

Because the laser energy is absorbed only in the selected area without affecting other organs, it is acting as a guidance to increase the heat by concentrating the RF current in the dermis while lowering the RF impedance. The laser beam of 915 nm is a suitable wave to develop the temperature of 45° C.~65° C. in the dermis, which is a good condition to reproduce the new cells without affecting other organs. The laser beam also renders synergy effects by combining with the RF energy and improving the hemoglobin passed through vacuum pressure. The dermis has a depth of approximately 0.5 mm~2.5 mm. The laser beam of 915 nm penetrates deeply enough into the dermis for reproducing new cells, for producing Collagen and Elastin and for combining the Chromophores of hemoglobin, RF energy and the Hemoglobin forcibly passed by the vacuum pressure.

As shown in FIG. 10, (d) the patient's skin is simultaneously stimulated and lifted by the suction process, while the high frequency wave of 1 MHz is illuminated onto the patient's skin through the electrodes. Through the above steps, the skin treatment is finished.

Figure 11:
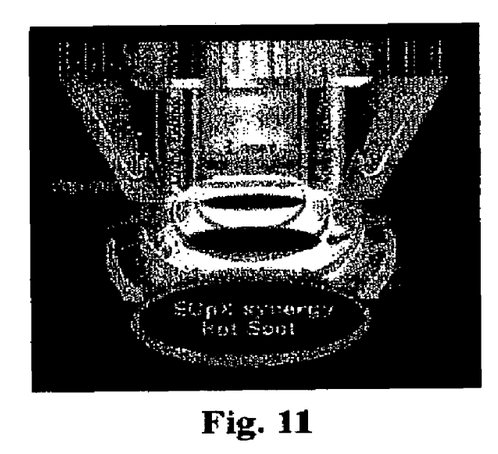
FIG. 11 is a mimetic diagram illustrating the overall technical process of the skin treatment of the present invention.

As shown in FIG. 11, the skin treatment of the present invention can maximize the treatment effect through the synergy among the vacuum pressure effect, cooling effect, optical energy effect, and stimulating effect by the high frequency wave.

Figure 12:
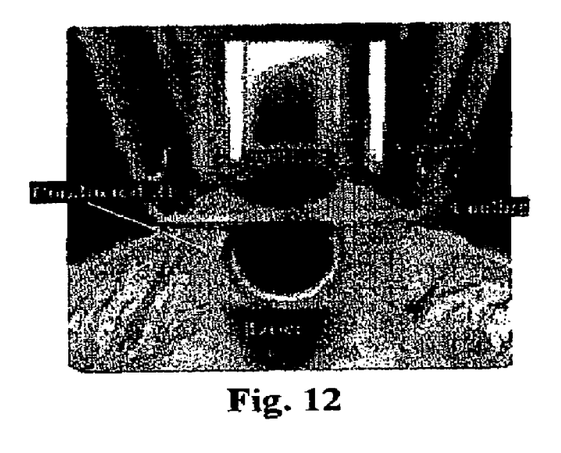
FIG. 12 is a mimetic diagram illustrating the formation of a hot spot relating to each step of the skin treatment of the present invention.

As shown in FIG. 12, the skin is lifted up to place between the electrodes through the suction process. Even if the suction process can remove the sebum, the present invention has an objective to reproduce new cells through producing the Collagen and Elastin in the dermis by emitting the RF high frequency while the skin is lifted up.

Accordingly, the suction process causes the Hemoglobin to collect at the treating area, thus it will accelerate the induction of the chromophore to improve the laser emitting effect.

At the same time, the electrode is cooled down for cooling the skin temperature while operating the suction process. Thus, the epidermis has a lower temperature in order to maintain a high skin resistance, while the dermis has a higher temperature for inducing a lower skin resistance. When the RF high frequency is emitted onto the patient's skin, more current of the RF high frequency flows through the dermis to form a hot spot. But, less current of the RF high frequency flows through the epidermis, helping to prevent burns.

For the next step, the near infrared laser beam is emitted into the area of chromophore concentration (passing near the blood vessel) formed through the suction process. The laser beam is focused on the area of chromophore concentration for developing the hot spot in the deep dermis. Because of the low skin resistance, it is possible to concentrate the RF high frequency effect.

Depending on the condition of the skin after treatment, (e) the red light in the range of 630 nm~660 nm may be emitted to the patient's skin. It is suitable to use the red light of 635 nm.

As aforementioned, the red light has a soothing effect to calm down the excited skin after the sucking and emitting of the high frequency rays. Because the red light has the effect of improving blood circulation, it will help to reproduce the new cells through continuous emitting after the treatment.

As discussed so far, the present invention adopts an applicator for the skin treatment devices in which the patient's skin is sucked up and placed between the pair of electrodes for treating by the high frequency rays. It improves the skin treatment, while eliminating discomfort and pain during the skin treatment.

According to the present invention, a cooling block is used for removing the heat generated by the pair of electrodes. Thus, it is possible that the emitted high frequency ray can deeply penetrate into the dermis through the suction and cooling processes. The pair of electrodes has each cooling block connected to the cooling unit for circulating coolant to control the temperature of the electrodes.

According to the present invention, it is possible to maximize the treatment effect by emitting the high frequency rays through the processes of cooling the epidermis and creating a hot spot in the deep dermis.

Further, the applicator of the present invention provides a soothing process after the skin treatment. Because the skin is exposed to stress and tension during the treatment by the emitted specific frequency waves, the relief process cures the skin cells to be stable, helps to produce new cells and prevents skin damage.

According to the present invention, an attachable applicator is provided to perform the various kinds of treatment by simply replacing the front tip of the applicator.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

What is claimed is:

1. An applicator attachable to a skin treatment device, which is capable to apply RF energy and optic energy simultaneously for treating a patient's skin, the attachable applicator comprising:

a housing (11) having a first mounting block (41) with a rear flange (41b) and a second mounting block (43) with a front annular groove (43a), wherein said first mounting block (41) consists of a tube plug (51a) having a first flow path (51) connected to a lateral vacuum pocket (25), said second mounting block (43) consists of an extension tube (53a) having a second flow path (53) for connecting to the first flow path (51) of the tube plug (51a), so that the rear flange (41b) of the first mounting block (41) is elastically coupled to the front annular groove (43a) of the second mounting block (43) for easily mounting to or off each other, an electrode (14) installed at a center of the housing (11) along with a longitudinal direction of an axis for generating high frequency radiation, so that said electrode (14) will be located above a swollen up skin, a capsule (23) forming a suction cavity (16) at an inlet portion, a lateral air-flow passage (21) and lateral vacuum pocket (25) disposed around the capsule (23) for sucking out the air from the suction cavity (16) to an inner chamber (17) being maintained a negative pressure by a vacuum unit, so that said capsule (23) is attached to or detached from said housing (11) for replacing different kind of capsule during the skin treatment, and a cooling unit (15) for removing excessive heat generated by the electrode (14) far maintaining a moderate treating temperature, wherein said cooling unit (15) has arranged a thermocouple (15a), which is tightly surrounding a pair of electrodes (14) and a cooling block (15b), which is tightly surrounding the thermocouple (15a).

2. An applicator attachable to a skin treatment device as claimed in claim 1, wherein said electrode (14) is a pair of rods arranged in parallel at the center of the housing (11) for emitting high frequency waves to treat the patient skin.

3. An applicator attachable to a skin treatment device as claimed in claim 1, wherein said electrode (14) is a single tube arranged inner core of the housing (11) for emitting high frequency waves to the patient skin.

4. An applicator attachable to a skin treatment device as claimed in claim 1, wherein said air flow passage (21) further comprising a filter (22) for filtering foreign objects being sucked from the patient skin.

5. An applicator attachable to a skin treatment device as claimed in claim 1, wherein said housing (11) further comprises a diode infrared laser (12) for emitting near infrared laser beams in the range of 800~1000 nm and a permeating element (13) installed in front of the diode infrared laser (12) for permeating the infrared laser beams.

6. An applicator attachable to a skin treatment device as claimed in claim 5, wherein said near infrared laser beam has a wavelength of about 915 nm.

7. An applicator attachable to a skin treatment device as claimed in claim 1, wherein said housing (11) further comprises a three-color emitting diode (31) obliquely installed lateral to the permeating element (13) for selectively emitting either blue, red or infrared light, and a reflecting element (32) installed opposite said three-color emitting diode (31) for reflecting the emitted light.

8. An applicator attachable to a skin treatment device as claimed in claim 7, wherein said three-color emitting diode (31) emits red light with a wavelength in the range of 630 nm to 640 nm.

9. An applicator attachable to a skin treatment device as claimed in claim 1, wherein said capsule (23) is alternatively formed a female thread (23*a*) at its inner rim for mating to a male thread (41*a*) formed at a front portion of the first mounting block (41), a front part of said second mounting block (43) is coupled to said first mounting block (41), and a rear part of said second mounting block (43) is coupled to said housing (11), so that said capsule (23) is mounted or removed from a tip portion of the hosing (11) for replacing different kind of capsule during the skin treatment.

10. An applicator attachable to a skin treatment device as claimed in claim 1, wherein said second mounting block (43) is alternatively formed with a rear annular groove (43*a*), and the front portion of the housing (11) is formed with a tip flange (11*a*) for elastically coupling to said rear annular groove (43*b*) of said second mounting block (43).

\* \* \* \* \*